US012324761B2

(12) United States Patent
Jielile et al.

(10) Patent No.: US 12,324,761 B2
(45) Date of Patent: Jun. 10, 2025

(54) NON-SURGICAL LENGTH-ADJUSTABLE REDUCTION EXERCISE THERAPY APPARATUS FOR RUPTURE OF ANTERIOR CRUCIATE LIGAMENT OR ACHILLES TENDON

(71) Applicant: Jiasharete Jielile, Urumqi (CN)

(72) Inventors: Jiasharete Jielile, Urumqi (CN);
Gulinuer Shabierhazi, Urumqi (CN);
Saizimu Halemhan, Urumqi (CN);
Muerzha Ayitimuhan, Urumqi (CN);
Naertai Yeerbo, Urumqi (CN);
Bayixiati Qianman, Urumqi (CN)

(73) Assignee: Jiasharete Jielile, Urumqi (CN)

( * ) Notice: Subject to any disclaimer, the term of this patent is extended or adjusted under 35 U.S.C. 154(b) by 674 days.

(21) Appl. No.: 17/720,170

(22) Filed: Apr. 13, 2022

(65) Prior Publication Data

US 2022/0339016 A1  Oct. 27, 2022

(30) Foreign Application Priority Data

Apr. 14, 2021  (CN) .......................... 202120757115.0

(51) Int. Cl.
*A61F 5/01* (2006.01)

(52) U.S. Cl.
CPC .......... *A61F 5/0111* (2013.01); *A61F 5/0125* (2013.01); *A61F 2005/0158* (2013.01); *A61F 2005/0197* (2013.01)

(58) Field of Classification Search
CPC .......... A61F 5/01; A61F 5/0102; A61F 5/012; A61F 5/0111; A61F 5/0113; A61F 5/0123; A61F 5/0125; A61F 5/0127; A61F 5/013; A61F 5/0193; A61F 5/05; A61F 5/0585; A61F 13/066; A61F 2005/0132; A61F 2005/0197; A61F 2007/0039; A61F 2007/0042; A61F 2007/0043; A61F 2007/0044; A61F 2007/0045; A61G 7/065; A61G 13/12; A61G 13/123; A43B 5/04; A43B 5/0409; A43B 5/0431; A43B 5/0433; A43B 5/1691; A43B 7/14

See application file for complete search history.

(56) References Cited

U.S. PATENT DOCUMENTS

2017/0231853 A1* 8/2017 Auger ...................... A61H 3/00
623/40

* cited by examiner

*Primary Examiner* — Alireza Nia
*Assistant Examiner* — Andrew Jun-Wai Mok
(74) *Attorney, Agent, or Firm* — J.C. PATENTS

(57) ABSTRACT

The present disclosure relates to a technical field of medical exercise apparatus. A non-surgical reduction exercise therapy apparatus for rupture of anterior cruciate ligament or achilles tendon includes a thigh immobilization device, a calf immobilization device, an adjustable knee joint hinge and a foot immobilization device, a boot heel being provided under a rear of the boot sole. The present disclosure has a reasonable and compact structure and is convenient to use, and also has characteristics of low treatment cost, no surgery, whole process activities, pleasant dance, no influence on work and study during treatment, and fast healing of the anterior cruciate ligament or achilles tendon.

16 Claims, 2 Drawing Sheets

NON-SURGICAL LENGTH-ADJUSTABLE REDUCTION EXERCISE THERAPY APPARATUS FOR RUPTURE OF ANTERIOR CRUCIATE LIGAMENT OR ACHILLES TENDON

CROSS-REFERENCE TO RELATED APPLICATION

This application claims priority to Chinese Patent Application No. 202120757115.0, filed on Apr. 14, 2021, which is hereby incorporated by reference in its entirety.

TECHNICAL FIELD

The present disclosure relates to a field of medical exercise apparatus technology, in particular, to a non-surgical length-adjustable reduction exercise therapy apparatus for rupture of anterior cruciate ligament or achilles tendon.

BACKGROUND

A treatment apparatus for anterior cruciate ligament or achilles tendon may be used for a treatment for a patient with rupture of anterior cruciate ligament or achilles tendon. Although the existing treatment apparatus may elevate a patient's heel, it cannot limit the flexion of a knee joint. While the patient is walking, his/her knee joint will always be in a straight position, and gastrocnemius muscle will endlessly stretch the anterior cruciate ligament or achilles tendon that is healing, causing the anterior cruciate ligament or the achilles tendon to be easily elongated. Furthermore, once cramp or fall occurs, the anterior cruciate ligament or achilles tendon will be further elongated or ruptured again, thus affecting the therapeutic effect of the anterior cruciate ligament or the achilles tendon. In addition, when the patient wears the existing apparatus for achilles tendon, an angle of plantar flexion will remain unchanged throughout the rehabilitation process, which is not conducive to the smooth growth and connection of the anterior cruciate ligament or the achilles tendon, thereby resulting in a slow healing speed of the cruciate ligament or the achilles tendon.

SUMMARY

Embodiments of the present disclosure provide a non-surgical reduction exercise therapy apparatus for rupture of anterior cruciate ligament or achilles tendon, which overcomes the deficiencies of the above-mentioned prior art and can be used to solve the problems of existing achilles tendon boots that the anterior cruciate ligament or the achilles tendon is easily stretched, the healing speed of the anterior cruciate ligament or the achilles tendon is slow, and the height of the patient's heel cannot be adjusted.

Technical solutions of the present disclosure are achieved by providing the following measures. A non-surgical length-adjustable reduction exercise therapy apparatus for rupture of anterior cruciate ligament or achilles tendon includes: a thigh immobilization device, a calf immobilization device, an adjustable knee joint hinge and a foot immobilization device, where the adjustable knee joint hinge is connected between the thigh immobilization device and the calf immobilization device to adjust and lock an angle between the thigh immobilization device and the calf immobilization device; the foot immobilization device includes a boot sole, a boot upper and an adjustable boot heel, the boot upper is provided on the boot sole, and the adjustable boot heel is provided under a rear of the boot sole; the adjustable boot heel includes a column-shaped fixed boot heel, a sleeve-shaped adjustment boot heel and a locking screw, a top of the fixed boot heel and a bottom of the rear of the boot sole are fixedly connected, an accommodation groove with an opened upper end and a closed lower end is formed in the adjustment boot heel, and a bottom of the fixed boot heel is inserted into the accommodation groove; at least two first adjustment and positioning holes are successively arranged at intervals from top to bottom on an outer wall of the fixed boot heel, at least two second adjustment and positioning holes are successively arranged at intervals from top to bottom in a penetrating manner on an outer wall of the adjustment boot heel corresponding to a position of the accommodation groove, the locking screw passes through the second adjustment and positioning hole and the first adjustment and positioning hole in sequence so as to make the fixed boot heel and the adjustment boot heel connected together, and the calf immobilization device and the boot upper are connected.

The following are further optimizations or/and improvements to the above-mentioned technical solutions of the present disclosure.

The above fixed boot heel may have a height of 5 cm to 8 cm, and the adjustment boot heel has a height of 6 cm to 9 cm, three first adjustment and positioning holes are successively and evenly arranged at intervals from top to bottom on the outer wall of the fixed boot heel, six second adjustment and positioning holes are successively and evenly arranged at intervals from top to bottom in a penetrating manner on the outer wall of the adjustment boot heel corresponding to the position of the accommodation groove, the distance between two adjacent first adjustment and positioning holes and the distance between two adjacent second adjustment and positioning holes are each 1 cm, and a compression spring is fixedly connected between the bottom of the fixed boot heel and a bottom wall of the accommodation groove.

A head of above boot sole may be flexible, a head of the boot upper is flexible, a fixed buckle is provided on an outer side of a middle of the boot upper, an elastic band is fixedly connected to an outer side of the head of the boot upper, and the elastic band and the fixed buckle are connected together.

The above boot sole may be anatomically bent upward in a direction of from a metatarsal toe portion to the boot heel to maintain a flexion of knee joint and ankle joint at 35 to 55 degrees.

The above calf immobilization device may include an upper calf sheath, a lower calf sheath, a press plate for tendon and a strip-shaped elastic bandage, the lower calf sheath is connected with the boot upper, the upper calf sheath and the lower calf sheath are connected by a length adjustment assembly to adjust and lock a distance between the upper calf sheath and the lower calf sheath, the upper calf sheath and the lower calf sheath that correspond to a rear position of calf are respectively provided with axially penetrating openings, the boot upper corresponding to a position of achilles tendon is provided with an axially penetrating opening, the press plate for tendon is in a shape of a curved plate that is matched with a gastrocnemius portion of the calf, two ends of the elastic bandage are connected by a hook-loop fastener to form a ring structure being capable of be bound on an outside of the gastrocnemius portion of the calf, the press plate for tendon is fixedly connected with the elastic bandage and capable of being tightly contact with a rear side of the gastrocnemius portion of the calf when the elastic bandage is bound on the outside of the gastrocnemius portion of the calf; the thigh immobilization device includes a thigh sheath, a portion of the thigh sheath corresponding to a rear position of the thigh being provided with an axially penetrating opening; an opening of the upper calf sheath, an opening of the lower calf sheath and an opening of the thigh sheath are respectively provided with a strap and a buckle at both sides; a first fixing rod is fixedly installed along a length direction on an outer side of the upper calf sheath corresponding to a left or right position of the calf, a second fixing rod is fixedly installed on an outer side of the thigh sheath corresponding to a position of the first fixing rod along the length direction, and the adjustable knee joint hinge is connected between the first fixing rod and the second fixing rod to adjust and lock an angle between the first fixing rod and the second fixing rod.

A lower end of the above lower calf sheath and an upper end of the boot upper may be fixedly connected or the lower calf sheath and the boot upper are connected by an ankle joint hinge to adjust and lock an angle between the lower calf sheath and the boot upper.

The above length adjustment assembly may include a plug-in rod, a length adjustment rod and a locking block, the plug-in rod is disposed on an outer side of an upper part of the lower calf sheath corresponding to the left or right position of the calf, a slot with an opening upper end being disposed in the plug-in rod; the length adjustment rod is disposed on an outer side of a lower part of the upper calf sheath corresponding to a position of the plug-in rod; the lower end of the length adjustment rod is inserted into the slot, the length adjustment rod is provided at intervals along a length direction with a number of locking grooves which are penetrated from left to right and each have forward opening; the locking block includes a rod-driving part and a rod-locking part, the rod-driving part is hinged on an outer side of the plug-in rod, one end of the rod-locking part is fixedly connected with the rod-driving part and is clamped in the locking groove, and the rod-locking part is capable of exiting out of the locking groove when the rod-driving part is turned; a guide rod is disposed on an outer side of the upper calf sheath corresponding to a position of the first fixing rod, in which a guide groove having an upper opening is disposed; a lower end of the first fixing rod is inserted in the guide groove; and the length adjustment rod, the plug-in rod, the first fixing rod and the guide rod are parallel to each other.

An achilles tendon shield is connected to a portion of the above lower calf sheath corresponding to a position of the achilles tendon through a fixing strap; and/or, a knee joint sheath is connected between the upper calf sheath and the thigh sheath, an upper end of the knee joint sheath is fixedly connected with a lower end of the thigh sheath, a lower end of the knee joint sheath is fixedly connected with an upper end of the upper calf sheath, and a portion of the knee joint sheath corresponding to a rear position of the knee joint is provided with an axially penetrating opening.

The present disclosure has a reasonable and compact structure, and is convenient to use. Firstly, it can ensure that the knee joint of patients having rupture of anterior cruciate ligament or achilles tendon is always in flexion state during pleasant walking, thereby preventing the anterior cruciate ligament or the achilles tendon from being stretched or broken again, and compressing repeatedly the anterior cruciate ligament or the achilles tendon, so as to make millions of distal and proximal horsetail-like not-completely broken ligaments or tendons to be fully return to its original position like crossed fingers and shortened and crossed, strive to make the anterior cruciate ligament or the achilles tendon shorten or close to normal length to heal, and avoid significantly prolonged healing caused by stretching of the anterior cruciate ligament or achilles tendon. At rest, flexion and extension activities of knee joint may be performed after further flexion of the knee joint. Secondly, through the setting of the adjustable boot heel, the height of heel can be flexibly adjusted during the rehabilitation process, so as to adjust the plantar flexion angle of the patient's knee and foot, which is conducive to the smooth growth and connection of the anterior cruciate ligament or the achilles tendon. Finally, since a surgery is not required for the patient, non-surgical operation can ensure that the original hematoma at the broken end of the anterior cruciate ligament or the achilles tendon will not be lost, because this original bleeding is the primary driving force for the healing of the anterior cruciate ligament or the achilles tendon. During the early dynamic compression treatment, the accumulated blood is widely squeezed and spread to thousands of shredded tendon bundles, which enlarges the uniform distribution of the original accumulated blood in healing area, thereby assisting in restoration and rapid healing under the mechanical and biological effects. It has the advantages of no hospitalization or short hospitalization time, low treatment cost, no surgery, whole process activities, pleasant dance, no influence on work and study during treatment, histologically directional healing of the anterior cruciate ligament or the achilles tendon, fast healing, few or no complications, comprehensive curative effect which is better than surgical treatment, no need for long-term sick leave, and no restriction on walking for commute.

Figure 1:
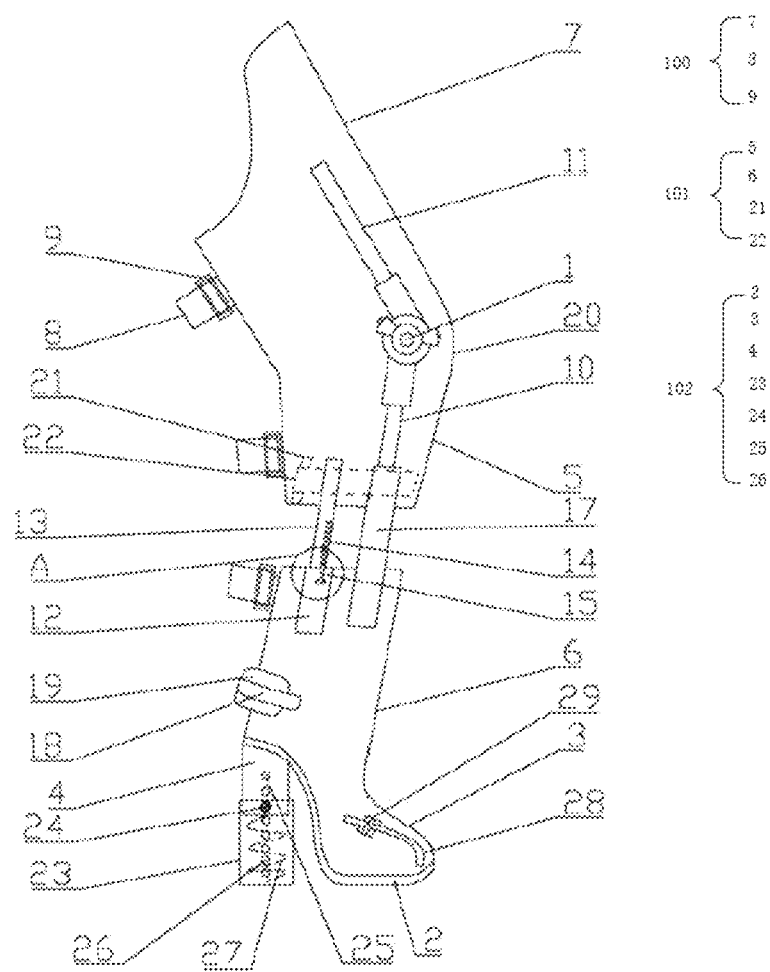
FIG. 1 is a structural schematic diagram according to a best embodiment of the present disclosure viewed from the left side.

Reference numbers in the drawings: 1: adjustable knee joint hinge; 2: boot sole; 3: boot upper; 4: fixed boot heel; 5: upper calf sheath; 6: lower calf sheath; 7: thigh sheath; 8: strap; 9: buckle; 10: first fixing rod; 11: second fixing rod; 12: plug-in rod; 13: length adjustment rod; 14: locking groove; 15: rod-driving part; 16: rod-locking part; 17: guide rod; 18: fixing strap; 19: achilles tendon shield; 20: knee joint sheath; 21: press plate for tendon; 22: elastic bandage; 23: adjustment boot heel; 24: locking screw; 25: first adjustment and positioning hole; 26: second adjustment and positioning hole; 27: compression spring; 28: elastic band; and 29: fixed buckle.

DESCRIPTION OF EMBODIMENTS

The present disclosure is not limited by the following embodiments, and the particular implementations can be determined according to technical solutions and actual conditions of the disclosure.

In the present disclosure, for the convenience of description, the relative positional relationship of respective components is described according to the layout of the FIG. 1 of the specification, For example, the positional relationships such as front, rear, upper, lower, left, right, etc. are determined according to the layout direction of the drawings in the specification.

Hereinafter, the present disclosure is further described with reference to the embodiments and drawings.

Figure 2:
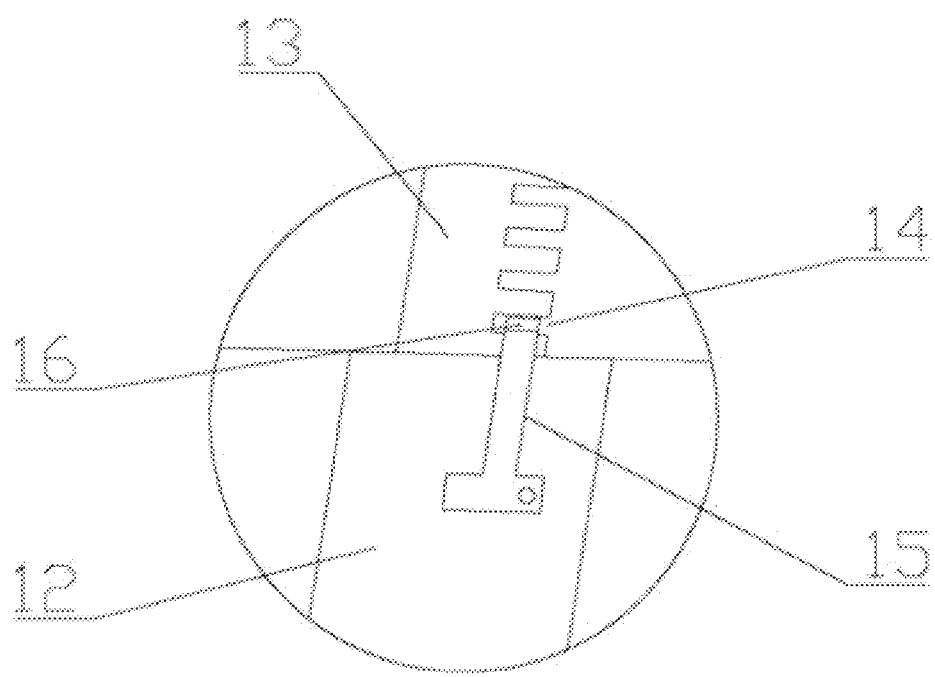
FIG. 2 is a structural schematic diagram of an enlarged structure at A in FIG. 1.

As shown in FIGS. 1 and 2, a non-surgical length-adjustable reduction exercise therapy apparatus for rupture of anterior cruciate ligament or achilles tendon includes: a thigh immobilization device 100, a calf immobilization device 101, an adjustable knee joint hinge 1 and a foot immobilization device 102. The adjustable knee joint hinge 1 is connected between the thigh immobilization device 100 and the calf immobilization device 101 to adjust and lock an angle between the thigh immobilization device 100 and the calf immobilization device 101. The foot immobilization device 102 includes: a boot sole 2, a boot upper 3 and an adjustable boot heel. The boot upper 3 is provided on the boot sole 2, and the adjustable boot heel is provided under the rear of the boot sole 2. The adjustable boot heel includes: a column-shaped fixed boot heel 4, a sleeve-shaped adjustment boot heel 23 and a locking screw 24. A top of the fixed boot heel 4 and the bottom of the rear of the boot sole 2 are fixedly connected together, an accommodation groove with an opened upper end and a closed lower end is formed in the adjustment boot heel 23, and a bottom of the fixed boot heel is inserted into the accommodation groove. At least two first adjustment and positioning holes 25 are successively arranged at intervals from top to bottom on an outer wall of the fixed boot heel 4, at least two second adjustment and positioning holes 26 are successively arranged, at intervals from top to bottom in a penetrating manner, on an outer wall of the adjustment boot heel 23 corresponding to a position of the accommodation groove, and the locking screw 24 passes through the second adjustment and positioning hole 26 and the first adjustment and positioning hole 25 in sequence so that the fixed boot heel 4 and the adjustment boot heel 23 are connected together. The calf immobilization device 101 and the boot upper 3 are connected.

As required, the adjustable knee joint hinge 1 belongs to the prior art, such as a structure of an adjustable knee joint hinge 1 disclosed by a patent application CN200820233634.1 and a patent application CN201120046105.2 respectively. In this embodiment, the adjustable knee joint hinge 1 may be a knee joint hinge with a model TJ005 that is produced by Dongguan Taijie Hardware Plastic Products Co., Ltd., its angle adjustment range being 0 degree to 120 degree. In other embodiments, the adjustable knee joint hinge 1 may be an adjustable knee joint hinge having other structures, specifically provided that it is capable of adjusting and locking an angle between the thigh immobilization device 100 and the calf immobilization device 101. The boot sole 2 is a soft boot sole. For example, the boot sole 2 may be made of any one material of PE, TPR, EVA, and rubber, and have certain deformability. The first adjustment and positioning hole is a threaded hole. One end of the locking screw passes through one of the second adjustment and positioning holes and then is screwed into one of the first adjustment and positioning holes so as to firmly connect the fixed boot heel with the adjustment boot heel together. When in use, for a patient with rupture injury of acute closed anterior cruciate ligament or achilles tendon or a patient after a surgery for rupture injury of the anterior cruciate ligament or the achilles tendon, a foot of the patient having ruptured anterior cruciate ligament or achilles tendon is firstly placed in the boot upper 3, and the patient's heel is put on the rear of the boot sole 2 and is lifted by the adjustable boot heel, with his toes being in a downward state, and then the calf immobilization device 101 and the thigh immobilization device 100 are fixed with the calf and thigh respectively. After that, the adjustable knee joint hinge 1 is adjusted to make the knee joint flex by 120°, at this time, the horsetail-like fiber bundles of the anterior cruciate ligament which are not completely broken in the knee joint are fully connected together, and then are arranged in parallel to heal. In addition, since the tendon on a back side of the calf is full and completely in a relaxed state, the achilles tendon will not be stretched and will be in a fully relaxed state when the patient is walking, which ensures that the achilles tendon bundles can be fully staggered and connected together to restore the conduction function of achilles tendon. It is implemented in such a manner that the achilles tendon and cruciate ligament may be compressed and healed within two months, and then gradually stretched and healed towards the distal end after two months. Both stages give full play to the mechanical and biological effects, which is conducive to the smooth growth and connection of the achilles tendon and cruciate ligament. In addition, through the setting of adjustable boot heel, the height of the whole adjustable boot heel may be adjusted according to the needs during treatment to realize the purpose of regulating the heel height, that is to realize the purpose of flexibly adjusting a flexion angle of the patient's knee and foot during the treatment, thereby being beneficial for the smooth growth and connection of the cruciate ligament and achilles tendon. This application has the characteristics of low treatment cost, no surgery, and flexibility in the whole process, no impact on work and study during the treatment, no need for long-term sick leave, no restriction on walking to and from work, and fast healing speed of cruciate ligament and achilles tendon.

According to actual requirement, the above-mentioned non-surgical length-adjustable reduction exercise therapy apparatus for rupture of anterior cruciate ligament or an achilles tendon can be further optimized and/or improved.

As shown in FIG. 1, the fixed boot heel has a height of 5 cm to 8 cm, and the adjustment boot heel has a height of 6 cm to 9 cm. Three first adjustment and positioning holes are successively and evenly arranged on the outer wall of the fixed boot heel at intervals from top to bottom, and six second adjustment and positioning holes are successively and evenly arranged at intervals in a penetrating manner on the outer wall of the adjustment boot heel corresponding to the position of the accommodation groove from top to bottom. The distance between two adjacent first adjustment and positioning holes and the distance between two adjacent second adjustment and positioning holes are each 1 cm, and a compression spring is fixedly connected between the bottom of the fixed boot heel and the bottom wall of the accommodation groove. According to requirements, in this embodiment, the height of the fixed boot heel is 6 cm and the height of the adjustment boot heel is 7 cm. Adjustment of the height of the entire adjustable boot heel can be achieved by locking the locking screw in the first adjustment and positioning hole and the second adjustment and positioning hole of different heights. The distance between two adjacent first adjustment and positioning holes and the distance between two adjacent second adjustment and positioning holes is each 1 cm, therefore, during the wearing treatment, the heel height of the patient may be evenly and gradually reduced by 1 cm per one stage through setting of the compression spring, and the flexion angle of the knee and ankle joint may be gradually reduced, which is further conducive to the smooth growth and connection of the cruciate ligament or achilles tendon.

As shown in FIG. 1, a head of boot sole 2 is flexible, a head of boot upper 3 is flexible, a fixed buckle 29 is provided on an outer side of the middle of the boot upper 3, an elastic band 28 is fixedly connected to an outer side of the head of boot upper 3, and the elastic band 28 and the fixed buckle 29 are connected together. According to requirements, both the soft boot sole and the soft boot upper are the prior art, for example, both of them may be made of leather or rubber. The fixed buckle 29 is the prior art, specifically provided that it can realize the snap-fit connection with the elastic band 28. Since the head of the boot sole 2 is a soft boot sole and the head of the boot upper 3 is a soft boot upper, the boot head of the present application may be stretched back and forth by adjustment of the elastic band 28 so as to be suitable for patients who has the different feet sizes to wear, thereby having a better applicability.

As shown in FIG. 1, the boot sole is anatomically bent upward from a metatarsal toe portion to the boot heel to maintain the flexion of the knee joint and ankle joint at 35 to 55 degrees. This ensures that the cruciate ligament or the achilles tendon is completely relaxed and will not be stretched when the patient wears and walks. In this embodiment, the boot sole is anatomically bent upward from a metatarsal toe portion to the heel to maintain the flexion of the knee joint and ankle joint at 35 to 55 degrees, it is believed in a non-surgical external fixation treatment that the angles of flexion of the knee joint and ankle joint determine the upward movement height of the stump of the anterior cruciate ligament of tibial intercondylar eminence, and/or the upward movement height of the achilles tendon at the stump of the calcaneal tubercle; the upward movement height of distal achilles tendon or the cruciate ligament determines the alignment density of broken end of the achilles tendon or the cruciate ligament. The tighter the staggered alignment of tendon bundles at the broken end of achilles tendon or ligament, the more ideal the recovery of the length of achilles tendon or cruciate ligament. As the length of achilles tendon or ligament is restored or shortened, the function of achilles tendon or cruciate ligament is restored in a more ideal manner. This is the idea that an angle determines a height and the height determines the length. When the knee joint is flexed about 30° or more, a distal broken end of the cruciate ligament moves upward and backward by 3-6 cm, so that the distal and proximal broken ends which are not completely disconnected are contacted completely, and the distal and proximal broken ends of the anterior cruciate ligament may be cross-embedded during repeated walking exercises. Likewise, when the ankle joint is flexed about 50° or more, a distal broken end of the achilles tendon moves upward and backward by 5-7 cm, so that the distal and proximal broken ends are contacted completely, and the distal and proximal broken ends of the achilles tendon may be cross-embedded during repeated walking exercises. The length of the achilles tendon is not basically restored, but basically shortened, and its peripheral diameter becomes bigger. Generally speaking, few patients can achieve up to 50° of initial passive plantar flexion of ankle joint. When the optimal plantar flexion angle is not reached, application of 8-week long-leg plaster fixation is difficult to restore the ruptured achilles tendon to its own length, or allow the ruptured achilles tendon to shorten to be chimeric, so it is necessary to repeat the walking practice to form the chimerism between the distal and proximal broken ends. During the movement, the cruciate ligaments that are not disconnected completely or torn tendon bundles of the achilles tendon are intercalated with each other, which not only increases the healing area, but also facilitates the realization of shortened length or near-normal reconstruction of the cruciate ligament or the achilles tendon.

As shown in FIGS. 1 and 2, the calf immobilization device 101 includes: an upper calf sheath 5, a lower calf sheath 6, a press plate for tendon 21 and a strip-shaped elastic bandage 22. The lower calf sheath 6 is connected with the boot upper 3, the upper calf sheath 5 and the lower calf sheath 6 are connected by a length adjustment assembly to adjust and lock a distance between the upper calf sheath 5 and the lower calf sheath 6. The upper calf sheath 5 and the lower calf sheath 6 that correspond to a rear position of the calf are respectively provided with axially penetrating openings. The boot upper 3 corresponding to the position of the achilles tendon is provided with an axially penetrating opening. The press plate for tendon 21 is in a shape of a curved plate that is matched with a gastrocnemius portion of an calf, and two ends of the elastic bandage 22 are connected by a hook-loop fastener to form a ring structure being capable of be bound on the outside of the gastrocnemius portion of the calf. The press plate for tendon 21 is fixedly connected with the elastic bandage 22 and may be tightly contact with the back of the calf gastrocnemius when the elastic bandage 22 is bound on the outside of the gastrocnemius portion of the calf. The thigh immobilization device 100 includes a thigh sheath 7, a portion of the thigh sheath corresponding to a rear position of the thigh being provided with an axially penetrating opening. The opening of the upper calf sheath 5, the opening of the lower calf sheath 6 and the opening of the thigh sheath 7 are respectively provided with a strap 8 and a buckle 9 at both sides. A first fixing rod 10 is fixedly installed along a length direction on an outer side of the upper calf sheath 5 corresponding to the left or right position of the calf, and a second fixing rod 11 is fixedly installed on an outer side of the thigh sheath 7 corresponding to the position of the first fixing rod 10 along the length direction. The adjustable knee joint hinge 1 is connected between the first fixing rod 10 and the second fixing rod 11 to adjust and lock an angle between the first fixing rod 10 and the second fixing rod 11.

According to requirements, the strap 8, the buckle 9 and the elastic bandage 22 belong to the prior art. For example, the strap 8 may be a hook-loop fastener, and the buckle 9 may be a buckle body in a shape of "同", the elastic bandage 22 is made of elastic material, both the upper calf sheath 5 and the lower calf sheath 6 are barrel-shaped structures which are matched with the calf, the thigh sheath 7 is a barrel-shaped structure which is matched with the thigh, and the upper calf sheath 5 is connected with the lower calf sheath 6 through the length adjustment assembly. In this way, it is suitable for patients of different heights to use and has wide applicability. The setting of openings is not only easy to wear, but also does not squeeze the achilles tendon, so that the achilles tendon is in the maximum physiological straight state as much as possible, so as to prevent the achilles tendon from being stretched due to the arc shape of the achilles tendon under pressure. When in use, the elastic bandage 22 is firstly bound to the outside of the calf gastrocnemius to make the press plate for tendon 21 tightly contact with the rear side of the calf gastrocnemius, and then the elastic bandage 22 corresponding to the front side of the calf gastrocnemius is pulled down obliquely towards the direction of the tip of boot. At this time, the press plate for tendon 21 will press down the tendon on the back side of the calf, and then the upper calf sheath 5, the lower calf sheath 6, and the thigh sheath 7 are fixedly sleeved on the upper part of the calf, the lower part of the calf, and the upper part of the thigh respectively through the straps 8. Since the first fixing rod 10 and the second fixing rod 11 are fixedly connected with the upper calf sheath 5 and the thigh sheath 7 respectively, the purpose of adjusting the knee flexion angle can be achieved by adjusting the angle between the first fixing rod 10 and the second fixing rod 11. During resting time, the strap 8 on the thigh sheath 7 may be loosened so as to further flex the knee joint by 10 degrees, and then carry out knee joint flexion and extension exercise, which not only prevents the stiffness of the knee joint, but also promotes the smooth healing of the anterior cruciate ligament under stress stimulation.

As shown in FIG. 1, a lower end of the lower calf sheath 6 and an upper end of the boot upper 3 are fixedly connected or the lower calf sheath 6 and the boot upper 3 are connected by an ankle joint hinge to adjust and lock an angle between the lower calf sheath 6 and the boot upper 3. The ankle joint hinge belongs to the prior art. In this embodiment, the lower end of the lower calf sheath 6 and the upper end of the boot upper 3 are fixedly connected, so that when the foot is lifted, the back of the foot bears fewer load, which facilitates the growth and connection of the anterior cruciate ligament or the achilles tendon. In other embodiment, the lower calf sheath 6 and the boot upper 3 may be connected by the ankle joint hinge.

As shown in FIGS. 1 and 2, the length adjustment assembly includes: a plug-in rod 12, a length adjustment rod 13 and a locking block. The plug-in rod 12 is disposed on an outer side of an upper part of the lower calf sheath 6 corresponding to the left or right position of the calf, and a slot with an opening upper end is disposed in the plug-in rod 12. The length adjustment rod 13 is disposed on an outer side of a lower part of the upper calf sheath 5 corresponding to the position of the plug-in rod 12, the lower end of the length adjustment rod 13 is inserted into the slot. The length adjustment rod 13 is provided at intervals along a length direction with a number of locking grooves 14 which are penetrated from left to right and have forward openings. The locking block includes a rod-driving part 15 and a rod-locking part 16, where the rod-driving part 15 is hinged on the outside of the plug-in rod 12, and one end of the rod-locking part 16 is fixedly connected with the rod-driving part 15 and is clamped in the locking groove 14. When the rod-driving part 15 is turned, the rod-locking part 16 may exit out of the locking groove 14. A guide rod 17 is disposed on the outer side of the upper calf sheath 5 corresponding to the position of the first fixing rod 10, in which a guide groove having an upper opening is disposed. The lower end of the first fixing rod 10 is inserted in the guide groove, and the length adjustment rod 13, the plug-in rod 12, the first fixing rod 10 and the guide rod 17 are parallel to each other. According to requirements, the width of the locking groove 14 is slightly larger than that of the rod-locking part 16, and the distance between two adjacent locking grooves 14 may be 0.5 cm. The purpose of adjusting and locking the distance between the upper calf sheath 5 and the lower calf sheath 6 is achieved through the arrangement of the plug-in rod 12, the length adjustment rod 13 and the locking block, thereby meeting the wearing requirements of patients of different heights. In addition, the setting of the guide rod 17 may prevent an offset between the upper calf sheath 5 and the lower calf sheath 6.

As shown in FIG. 1, an achilles tendon shield 19 is connected to a portion of the lower calf sheath 6 corresponding to the position of the achilles tendon through a fixing strap18; and/or, a knee joint sheath 20 is connected between the upper calf sheath 5 and the thigh sheath 7. An upper end of the knee joint sheath 20 is fixedly connected with a lower end of the thigh sheath 7, and a lower end of the knee joint sheath 20 is fixedly connected with an upper end of the upper calf sheath 5. The knee joint sheath 20 corresponding to the rear side of the knee joint is provided with an axially penetrating opening. According to requirements, the upper calf sheath 5, the thigh sheath 7, and the knee joint sheath 20 are integrally formed, and may be made of leather or other soft materials. In Kazakh folks, a non-surgical treatment of bifurcated branches for fixation of medial and lateral flexion of the knee and ankle is performed on the person having the anterior cruciate ligament that is not completely torn or the rupture of achilles tendon. Because of the support of the forked branches under the heel, they can move in a small range in a short time. Due to the support of forked branches under the heel, it is possible to move in a small range in a short time. Through the arrangement of the lower calf sheath 6, the upper calf sheath 5, the thigh sheath 7, the knee joint sheath 20, the boot heel and other structures, the disclosure is equivalent to the lengthening and heightening design of the traditional Kazakh riding boots, so as to realize the non-surgical reduction of the rupture injury of the anterior cruciate ligament or achilles tendon, and the pleasant exercise treatment. Through the arrangement of the achilles tendon shield 19, the achilles tendon may be prevented from secondary trauma.

The above technical features constitute the best embodiment of the present disclosure, which has relatively strong adaptability and best implementation effect, and can increase or decrease unnecessary technical features according to actual needs to meet the needs of different situations.

What is claimed is:

1. A non-surgical length-adjustable reduction exercise therapy apparatus for rupture of anterior cruciate ligament or achilles tendon, comprising: a thigh immobilization device, a calf immobilization device, an adjustable knee joint hinge and a foot immobilization device, wherein the adjustable knee joint hinge is connected between the thigh immobilization device and the calf immobilization device to adjust and lock an angle between the thigh immobilization device and the calf immobilization device; the foot immobilization device comprises a boot sole, a boot upper and an adjustable boot heel, the boot upper is provided on the boot sole, and the adjustable boot heel is provided under a rear of the boot sole; the adjustable boot heel comprises a column-shaped fixed boot heel, a sleeve-shaped adjustment boot heel and a locking screw, a top of the column-shaped fixed boot heel and a bottom of the rear of the boot sole are fixedly connected, an accommodation groove with an opened upper end and a closed lower end is formed in the adjustment boot heel, and a bottom of the column-shaped fixed boot heel is inserted into the accommodation groove; at least two first adjustment and positioning holes are successively arranged at intervals from top to bottom on an outer wall of the column-shaped fixed boot heel, at least two second adjustment and positioning holes are successively arranged at intervals from top to bottom in a penetrating manner on an outer wall of the adjustment boot heel corresponding to a position of the accommodation groove, the locking screw passes through the at least two second adjustment and positioning holes and the at least two first adjustment and positioning holes in sequence so as to make the column-shaped fixed boot heel and the adjustment boot heel connected together, and the calf immobilization device and the boot upper are connected.

2. The non-surgical length-adjustable reduction exercise therapy apparatus for rupture of anterior cruciate ligament or achilles tendon according to claim 1, wherein the column-shaped fixed boot heel has a height of 5 cm to 8 cm, and the adjustment boot heel has a height of 6 cm to 9 cm, three first adjustment and positioning holes are successively and evenly arranged at intervals from top to bottom on the outer wall of the column-shaped fixed boot heel, six second adjustment and positioning holes are successively and evenly arranged at intervals from top to bottom in a penetrating manner on the outer wall of the adjustment boot heel corresponding to the position of the accommodation groove, the distance between two adjacent first adjustment and positioning holes and the distance between two adjacent second adjustment and positioning holes are each 1 cm, and a compression spring is fixedly connected between the bottom of the column-shaped fixed boot heel and a bottom wall of the accommodation groove.

3. The non-surgical length-adjustable reduction exercise therapy apparatus for rupture of anterior cruciate ligament or achilles tendon according to claim 2, wherein the calf immobilization device comprises an upper calf sheath, a lower calf sheath, a press plate for tendon and a strip-shaped elastic bandage, the lower calf sheath is connected with the boot upper, the upper calf sheath and the lower calf sheath are connected by a length adjustment assembly to adjust and lock a distance between the upper calf sheath and the lower calf sheath, the upper calf sheath and the lower calf sheath that correspond to a rear position of a calf are respectively provided with axially penetrating openings, the boot upper corresponding to a position of achilles tendon is provided with an axially penetrating opening, the press plate for tendon is in a shape of a curved plate that is matched with a gastrocnemius portion of the calf, two ends of the elastic bandage are connected by a hook-loop fastener to form a ring structure being capable of be bound on an outside of the gastrocnemius portion of the calf, the press plate for tendon is fixedly connected with the elastic bandage and capable of being tightly contact with a rear side of the gastrocnemius portion of the calf when the elastic bandage is bound on the outside of the gastrocnemius portion of the calf; the thigh immobilization device comprises a thigh sheath, a portion of the thigh sheath corresponding to a rear position of a thigh being provided with an axially penetrating opening; an opening of the upper calf sheath, an opening of the lower calf sheath and an opening of the thigh sheath are respectively provided with a strap and a buckle at both sides; a first fixing rod is fixedly installed along a length direction on an outer side of the upper calf sheath corresponding to a left or right position of the calf, a second fixing rod is fixedly installed on an outer side of the thigh sheath corresponding to a position of the first fixing rod along the length direction, and the adjustable knee joint hinge is connected between the first fixing rod and the second fixing rod to adjust and lock an angle between the first fixing rod and the second fixing rod.

4. The non-surgical length-adjustable reduction exercise therapy apparatus for rupture of anterior cruciate ligament or achilles tendon according to claim 3, wherein a lower end of the lower calf sheath and an upper end of the boot upper are fixedly connected or the lower calf sheath and the boot upper are connected by an ankle joint hinge to adjust and lock an angle between the lower calf sheath and the boot upper.

5. The non-surgical length-adjustable reduction exercise therapy apparatus for rupture of anterior cruciate ligament or achilles tendon according to claim 4, wherein the length adjustment assembly comprises a plug-in rod, a length adjustment rod and a locking block, the plug-in rod is disposed on an outer side of an upper part of the lower calf sheath corresponding to the left or right position of the calf, a slot with an opening upper end being disposed in the plug-in rod; the length adjustment rod is disposed on an outer side of a lower part of the upper calf sheath corresponding to a position of the plug-in rod; the lower end of the length adjustment rod is inserted into the slot, the length adjustment rod is provided at intervals along a length direction with a number of locking grooves which are penetrated from left to right and each have forward opening; the locking block comprises a rod-driving part and a rod-locking part, the rod-driving part is hinged on an outer side of the plug-in rod, one end of the rod-locking part is fixedly connected with the rod-driving part and is clamped in the locking groove, and the rod-locking part is capable of exiting out of the locking groove when the rod-driving part is turned; a guide rod is disposed on an outer side of the upper calf sheath corresponding to a position of the first fixing rod, in which a guide groove having an upper opening is disposed; a lower end of the first fixing rod is inserted in the guide groove; and the length adjustment rod, the plug-in rod, the first fixing rod and the guide rod are parallel to each other.

6. The non-surgical length-adjustable reduction exercise therapy apparatus for rupture of anterior cruciate ligament or achilles tendon according to claim 4, wherein an achilles tendon shield is connected to a portion of the lower calf sheath corresponding to a position of the achilles tendon through a fixing strap; and/or, a knee joint sheath is connected between the upper calf sheath and the thigh sheath, an upper end of the knee joint sheath is fixedly connected with a lower end of the thigh sheath, a lower end of the knee joint sheath is fixedly connected with an upper end of the upper calf sheath, and a portion of the knee joint sheath corresponding to a rear position of the knee joint is provided with an axially penetrating opening.

7. The non-surgical length-adjustable reduction exercise therapy apparatus for rupture of anterior cruciate ligament or achilles tendon according to claim 3, wherein the length adjustment assembly comprises a plug-in rod, a length adjustment rod and a locking block, the plug-in rod is disposed on an outer side of an upper part of the lower calf sheath corresponding to the left or right position of the calf, a slot with an opening upper end being disposed in the plug-in rod; the length adjustment rod is disposed on an outer side of a lower part of the upper calf sheath corresponding to a position of the plug-in rod; the lower end of the length adjustment rod is inserted into the slot, the length adjustment rod is provided at intervals along a length direction with a number of locking grooves which are penetrated from left to right and each have forward opening; the locking block comprises a rod-driving part and a rod-locking part, the rod-driving part is hinged on an outer side of the plug-in rod, one end of the rod-locking part is fixedly connected with the rod-driving part and is clamped in the locking groove, and the rod-locking part is capable of exiting out of the locking groove when the rod-driving part is turned; a guide rod is disposed on an outer side of the upper calf sheath corresponding to a position of the first fixing rod, in which a guide groove having an upper opening is disposed; a lower end of the first fixing rod is inserted in the guide groove; and the length adjustment rod, the plug-in rod, the first fixing rod and the guide rod are parallel to each other.

8. The non-surgical length-adjustable reduction exercise therapy apparatus for rupture of anterior cruciate ligament or achilles tendon according to claim 3, wherein an achilles tendon shield is connected to a portion of the lower calf sheath corresponding to a position of the achilles tendon through a fixing strap; and/or, a knee joint sheath is connected between the upper calf sheath and the thigh sheath, an upper end of the knee joint sheath is fixedly connected with a lower end of the thigh sheath, a lower end of the knee joint sheath is fixedly connected with an upper end of the upper calf sheath, and a portion of the knee joint sheath corresponding to a rear position of the knee joint is provided with an axially penetrating opening.

9. The non-surgical length-adjustable reduction exercise therapy apparatus for rupture of anterior cruciate ligament or achilles tendon according to claim 1, wherein the calf immobilization device comprises an upper calf sheath, a lower calf sheath, a press plate for tendon and a strip-shaped elastic bandage, the lower calf sheath is connected with the boot upper, the upper calf sheath and the lower calf sheath are connected by a length adjustment assembly to adjust and lock a distance between the upper calf sheath and the lower calf sheath, the upper calf sheath and the lower calf sheath that correspond to a rear position of a calf are respectively provided with axially penetrating openings, the boot upper corresponding to a position of achilles tendon is provided with an axially penetrating opening, the press plate for tendon is in a shape of a curved plate that is matched with a gastrocnemius portion of the calf, two ends of the elastic bandage are connected by a hook-loop fastener to form a ring structure being capable of be bound on an outside of the gastrocnemius portion of the calf, the press plate for tendon is fixedly connected with the elastic bandage and capable of being tightly contact with a rear side of the gastrocnemius portion of the calf when the elastic bandage is bound on the outside of the gastrocnemius portion of the calf; the thigh immobilization device comprises a thigh sheath, a portion of the thigh sheath corresponding to a rear position of a thigh being provided with an axially penetrating opening; an opening of the upper calf sheath, an opening of the lower calf sheath and an opening of the thigh sheath are respectively provided with a strap and a buckle at both sides; a first fixing rod is fixedly installed along a length direction on an outer side of the upper calf sheath corresponding to a left or right position of the calf, a second fixing rod is fixedly installed on an outer side of the thigh sheath corresponding to a position of the first fixing rod along the length direction, and the adjustable knee joint hinge is connected between the first fixing rod and the second fixing rod to adjust and lock an angle between the first fixing rod and the second fixing rod.

10. The non-surgical length-adjustable reduction exercise therapy apparatus for rupture of anterior cruciate ligament or achilles tendon according to claim 9, wherein a lower end of the lower calf sheath and an upper end of the boot upper are fixedly connected or the lower calf sheath and the boot upper are connected by an ankle joint hinge to adjust and lock an angle between the lower calf sheath and the boot upper.

11. The non-surgical length-adjustable reduction exercise therapy apparatus for rupture of anterior cruciate ligament or achilles tendon according to claim 10, wherein the length adjustment assembly comprises a plug-in rod, a length adjustment rod and a locking block, the plug-in rod is disposed on an outer side of an upper part of the lower calf sheath corresponding to the left or right position of the calf, a slot with an opening upper end being disposed in the plug-in rod; the length adjustment rod is disposed on an outer side of a lower part of the upper calf sheath corresponding to a position of the plug-in rod; the lower end of the length adjustment rod is inserted into the slot, the length adjustment rod is provided at intervals along a length direction with a number of locking grooves which are penetrated from left to right and each have forward opening; the locking block comprises a rod-driving part and a rod-locking part, the rod-driving part is hinged on an outer side of the plug-in rod, one end of the rod-locking part is fixedly connected with the rod-driving part and is clamped in the locking groove, and the rod-locking part is capable of exiting out of the locking groove when the rod-driving part is turned; a guide rod is disposed on an outer side of the upper calf sheath corresponding to a position of the first fixing rod, in which a guide groove having an upper opening is disposed; a lower end of the first fixing rod is inserted in the guide groove; and the length adjustment rod, the plug-in rod, the first fixing rod and the guide rod are parallel to each other.

12. The non-surgical length-adjustable reduction exercise therapy apparatus for rupture of anterior cruciate ligament or achilles tendon according to claim 10, wherein an achilles tendon shield is connected to a portion of the lower calf sheath corresponding to a position of the achilles tendon through a fixing strap; and/or, a knee joint sheath is connected between the upper calf sheath and the thigh sheath, an upper end of the knee joint sheath is fixedly connected with a lower end of the thigh sheath, a lower end of the knee joint sheath is fixedly connected with an upper end of the upper calf sheath, and a portion of the knee joint sheath corresponding to a rear position of the knee joint is provided with an axially penetrating opening.

13. The non-surgical length-adjustable reduction exercise therapy apparatus for rupture of anterior cruciate ligament or achilles tendon according to claim 9, wherein the length adjustment assembly comprises a plug-in rod, a length adjustment rod and a locking block, the plug-in rod is disposed on an outer side of an upper part of the lower calf sheath corresponding to the left or right position of the calf, a slot with an opening upper end being disposed in the plug-in rod; the length adjustment rod is disposed on an outer side of a lower part of the upper calf sheath corresponding to a position of the plug-in rod; the lower end of the length adjustment rod is inserted into the slot, the length adjustment rod is provided at intervals along a length direction with a number of locking grooves which are penetrated from left to right and each have forward opening; the locking block comprises a rod-driving part and a rod-locking part, the rod-driving part is hinged on an outer side of the plug-in rod, one end of the rod-locking part is fixedly connected with the rod-driving part and is clamped in the locking groove, and the rod-locking part is capable of exiting out of the locking groove when the rod-driving part is turned; a guide rod is disposed on an outer side of the upper calf sheath corresponding to a position of the first fixing rod, in which a guide groove having an upper opening is disposed; a lower end of the first fixing rod is inserted in the guide groove; and the length adjustment rod, the plug-in rod, the first fixing rod and the guide rod are parallel to each other.

14. The non-surgical length-adjustable reduction exercise therapy apparatus for rupture of anterior cruciate ligament or achilles tendon according to claim 9, wherein an achilles tendon shield is connected to a portion of the lower calf sheath corresponding to a position of the achilles tendon through a fixing strap; and/or, a knee joint sheath is connected between the upper calf sheath and the thigh sheath, an upper end of the knee joint sheath is fixedly connected with a lower end of the thigh sheath, a lower end of the knee joint sheath is fixedly connected with an upper end of the upper calf sheath, and a portion of the knee joint sheath corresponding to a rear position of the knee joint is provided with an axially penetrating opening.

15. The non-surgical length-adjustable reduction exercise therapy apparatus for rupture of anterior cruciate ligament or achilles tendon according to claim 1, wherein a head of the boot sole is flexible, a head of the boot upper is flexible, a fixed buckle is provided on an outer side of a middle of the boot upper, an elastic band is fixedly connected to an outer side of the head of the boot upper, and the elastic band and the fixed buckle are connected together.

16. The non-surgical length-adjustable reduction exercise therapy apparatus for rupture of anterior cruciate ligament or achilles tendon according to claim 1, wherein the boot sole is anatomically bent upward in a direction of from a metatarsal toe portion to the adjustable boot heel to maintain a flexion of knee joint and ankle joint at 35 to 55 degrees.

* * * * *